United States Patent [19]

Taheri

[11] Patent Number: 5,035,702
[45] Date of Patent: Jul. 30, 1991

[54] METHOD AND APPARATUS FOR PROVIDING AN ANASTOMOSIS

[76] Inventor: Syde A. Taheri, 268 Dan Troy, Williamsville, N.Y. 14221

[21] Appl. No.: 539,583

[22] Filed: Jun. 18, 1990

[51] Int. Cl.⁵ ............................................. A61B 17/00
[52] U.S. Cl. .................................... 606/153; 606/220
[58] Field of Search .............................. 606/151–153, 606/220

[56] References Cited

U.S. PATENT DOCUMENTS

| | | | |
|---|---|---|---|
| 3,316,914 | 5/1967 | Collito | 606/153 |
| 4,154,241 | 5/1979 | Rudie | 606/153 |
| 4,294,255 | 10/1981 | Geroc | 606/153 |
| 4,523,592 | 6/1985 | Daniel | 606/153 |
| 4,577,631 | 3/1986 | Kreamer | 606/156 |

Primary Examiner—Stephen C. Pellegrino
Assistant Examiner—Gary Jackson
Attorney, Agent, or Firm—Sommer, Oliverio & Sommer

[57] ABSTRACT

An improved portal-caval shunt (20) includes a male section (25) and a female section (26). A cutter (52) is first inserted through a patient's vena cava and is used to punch or cut an opening between proximate portions of the vena cava and portal vein. The female section (26) is then inserted through the opening. Once so inserted, spokes (36') on the female section move to their outward positions. The male section (25) is then inserted through the vena cava, is aligned with, and is joined to the female section, with its spokes (36) being aligned with the female section spokes (36'). The improved shunt is particularly useful in relieving a portal hypertension condition.

18 Claims, 3 Drawing Sheets

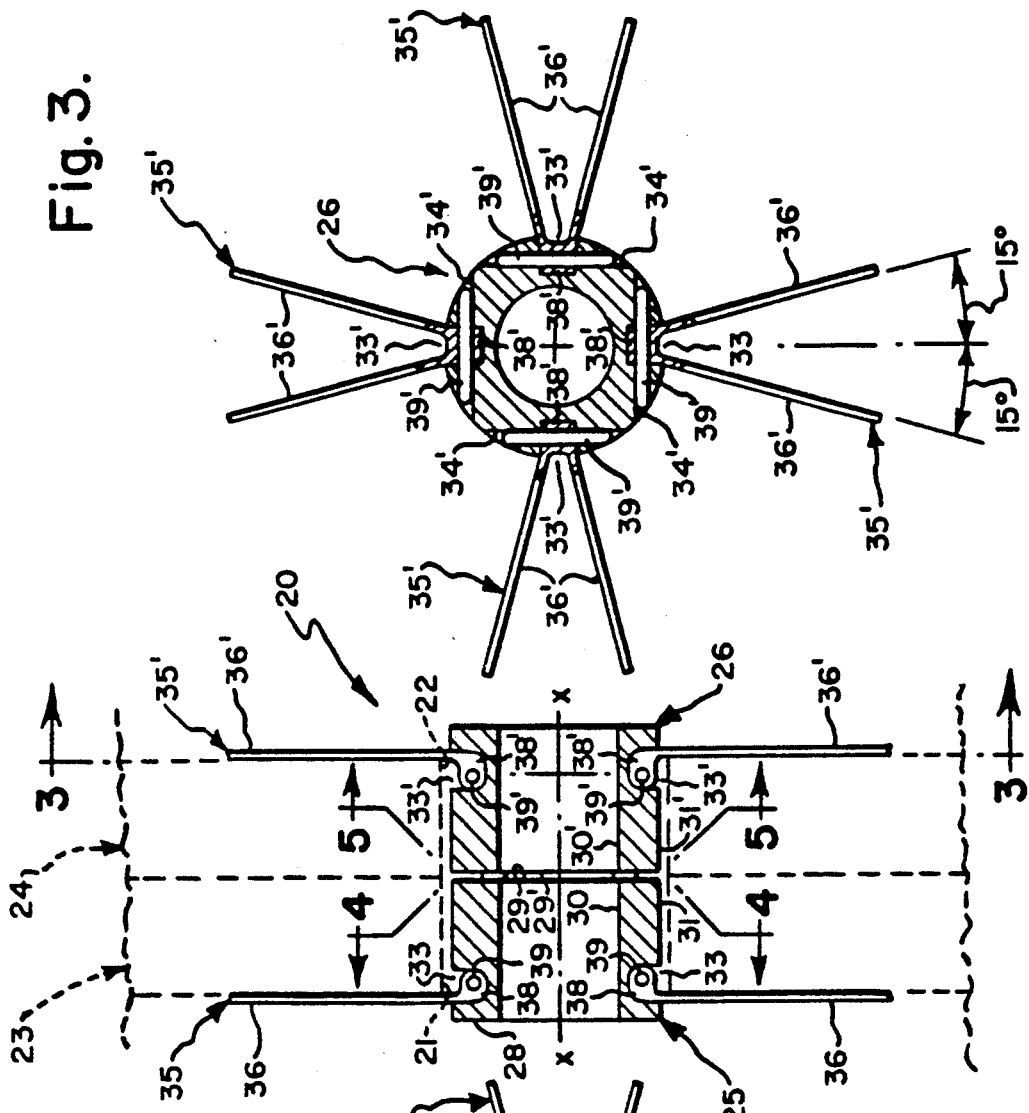

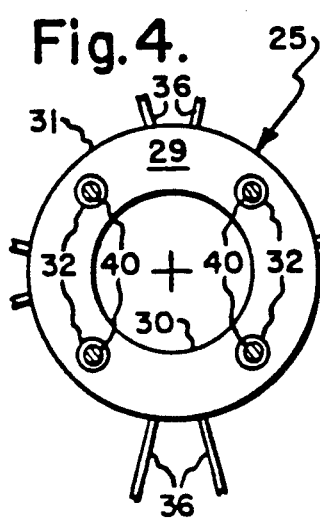
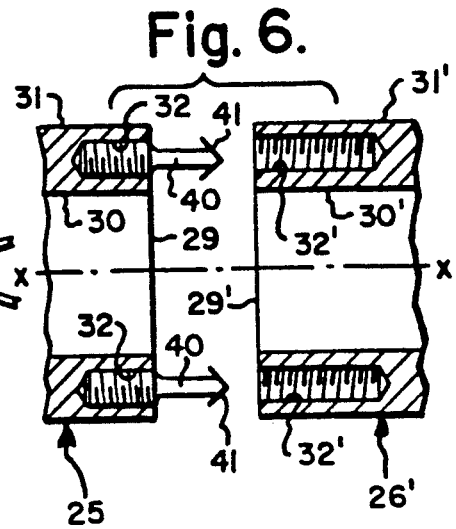
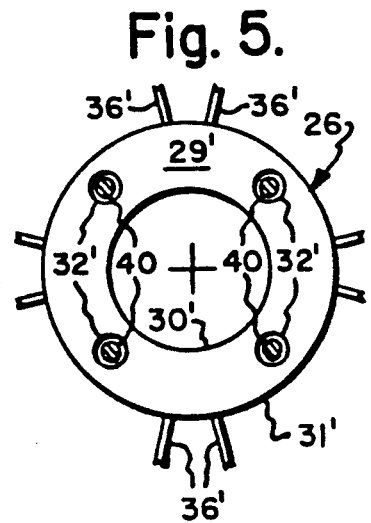
Fig. 4.  Fig. 6.  Fig. 5.
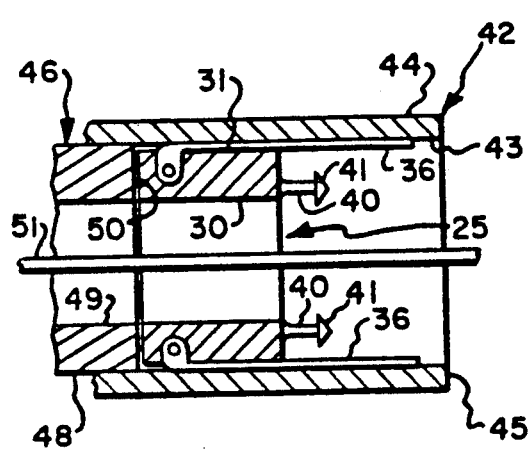
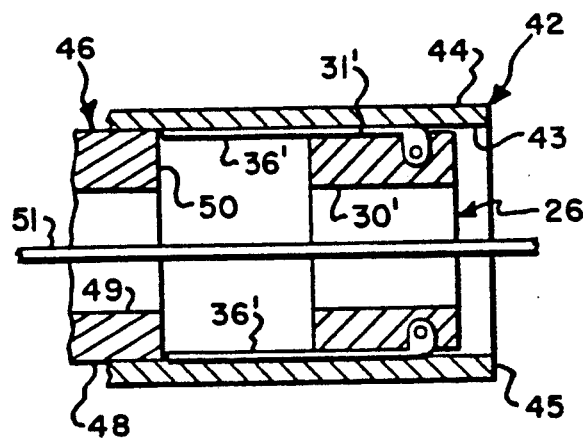
Fig. 7.  Fig. 8.
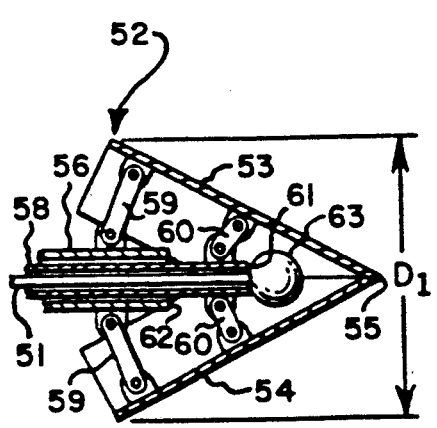
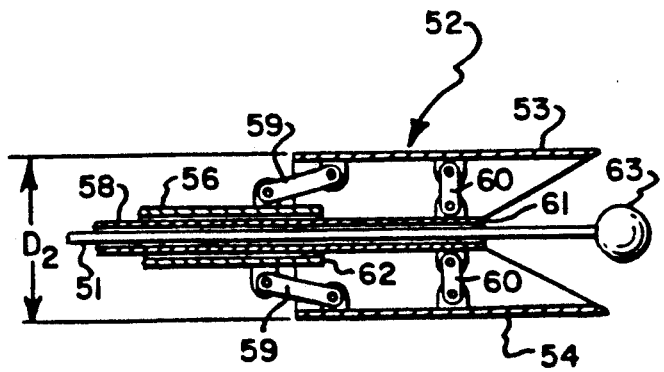
Fig. 9.  Fig. 10.

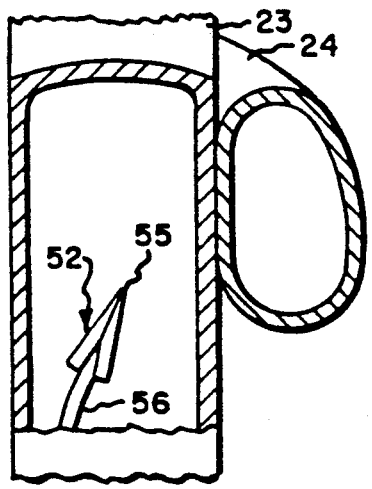
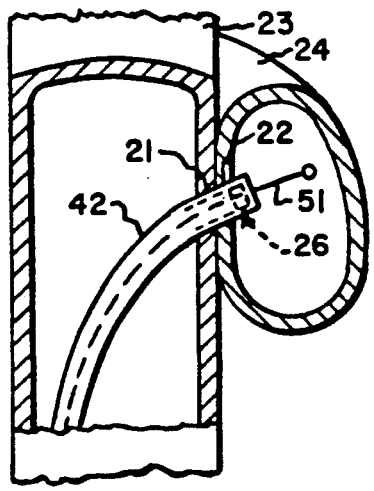
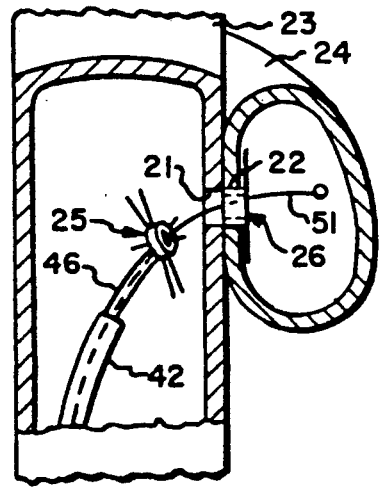
Fig. 11.    Fig. 14.    Fig. 17.
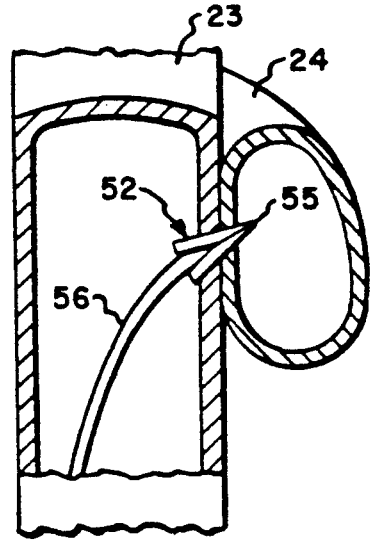
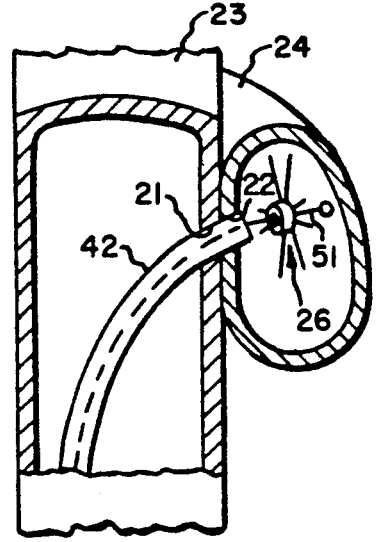
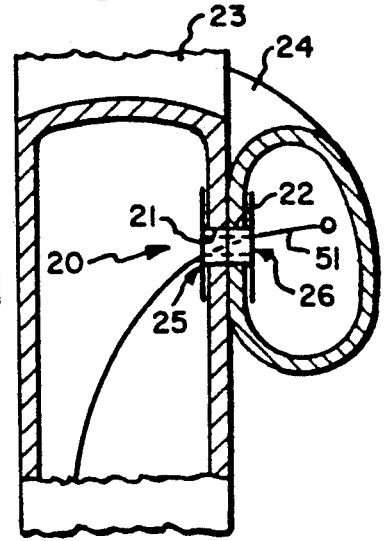
Fig. 12.    Fig. 15.    Fig. 18.
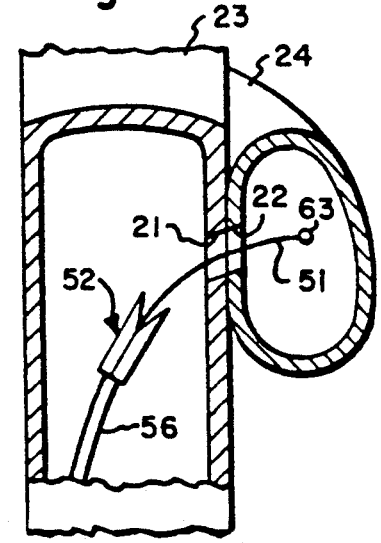
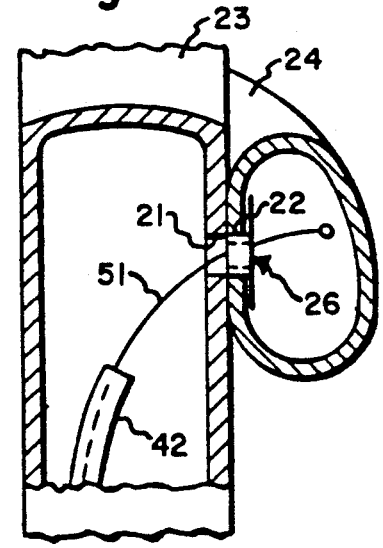
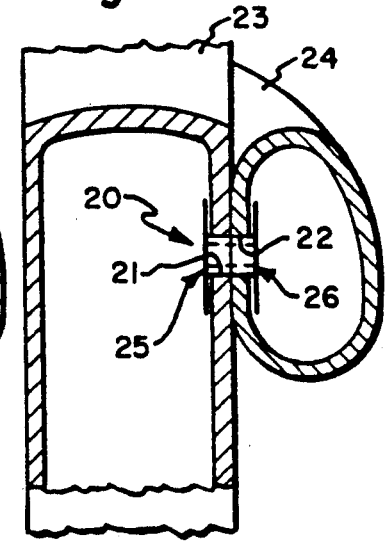
Fig. 13.    Fig. 16.    Fig. 19.

5,035,702

METHOD AND APPARATUS FOR PROVIDING AN ANASTOMOSIS

TECHNICAL FIELD

This invention relates generally to a method and apparatus for providing an anastomosis, and, more particularly, to an improved portal-caval shunt and to an improved method of relieving portal hypertension.

BACKGROUND ART

It is sometimes desired to relieve a condition known as portal hypertension. This condition is characterized by the pressure of blood in the portal vein being substantially greater than its normal pressure. In some cases, this condition is relieved surgically, with the surgeon first making a major incision in the body, then making an opening between proximate portions of the vena cava and portal vein, and thereafter suturing marginal portions of such vessels together about the surgically-formed opening. The intent here is to provide a shunt to relieve excess pressure in the portal vein to the patient's vena cava. This technique, while effective, requires major surgery.

Accordingly, there is believed to be a need for an improved device that would permit the provision of a anastomotic shunt, for example to relieve portal hypertension, without the need for major surgery.

DISCLOSURE OF THE INVENTION

With parenthetical reference to the corresponding parts or portions of the disclosed embodiment for the purposes of illustration, this invention provides, in one aspect, an improved anastomotic shunt (20) which broadly includes: an open-ended tubular male section (25); an open-ended tubular female section (26); each of said sections having a plurality of spokes (36,36', respectively); each of said spokes being adapted to moved between an extended position (i.e., as shown in FIGS. 2 and 3) at which the spoke extends outwardly from the associated section, and a retracted position (i.e., as shown in FIGS. 7 and 8) at which the spoke is positioned along side the associated section; and joining means (40,32') for joining the male and female sections together so as to create a passageway (30,30') therewithin; whereby the sections may be positioned in an opening jointing two tubular vessels (e.g., the vena cava and portal vein) and may be joined together with the spokes being in the extended positions to hold marginal portions of the vessels about the openings together, to provide a shunt between the vessels.

In another aspect, the invention provides an improved method of providing an anastomotic shunt between two tubular vessels (i.e., the vena cava and portal vein), which method includes the steps of: inserting a cutter head (52) longitudinally into one of the vessels (e.g., the patient's vena cava); pushing the cutter head and a stylet (51) carried thereby through the walls of the vessels to provide openings (21,22) therein; withdrawing the cutter head back along the stylet; positioning a first member (26) having a plurality of spokes (36') mounted for movement between extended and retracted positions, on the stylet; holding the first member spokes in their retracted positions; inserting the first member along the stylet through one vessel (e.g., the patient's vena cava) and through the openings into the other vessel (e.g., the portal vein); moving the first member spokes to their extended positions; positioning a second member (25) having a plurality of spokes (36) mounted for movement between extended positions and retracted positions on the stylet; holding the second member spokes in their retracted positions; inserting the second member along the stylet through the one vessel (e.g., the vena cava); moving the second member spokes to their extended positions within the one vessel; joining the first and second members such that marginal portions of the vessels about the openings will be compressively held together by the spokes; and removing the stylet; thereby to form an anastomotic shunt between the two vessels.

Accordingly, the general object of this invention is to provide an improved anastomotic shunt.

Another object is to provide an improved method of providing an anastomotic shunt.

Another object is to provide an improved method and apparatus for relieving portal hypertension.

These and other objects and advantages will become apparent from the foregoing and ongoing written specification, the drawings, and the appended claims.

BRIEF DESCRIPTION OF THE DRAWINGS

FIG. 1 is a fragmentary longitudinal vertical sectional view of one form of the improved shunt, showing the male and female sections as being operatively coupled together with the spokes extending generally radially outwardly from the axis of the shunt to embrace marginal portions of the portal vein and vena cava about the opening to provide an anastomosis therebetween.

FIG. 2 is a left end elevation of the leftward male section, this view showing the spokes as extending outwardly from the male section.

FIG. 3 is a fragmentary transverse vertical sectional view thereof, taken generally on line 3—3 of FIG. 1, showing the manner by which the spokes are pivotally connected to the female section.

FIG. 4 is fragmentary transverse vertical sectional view thereof, taken generally on line 4—4 of FIG. 1, showing the right end face of the male section in elevation.

FIG. 5 is a fragmentary transverse vertical sectional view thereof, taken generally on line 5—5 of FIG. 1, showing the left end face of the female section in elevation.

FIG. 6 is a fragmentary longitudinal exploded aligned vertical sectional view showing the male section pins as being aligned with the female section recesses, prior of joinder of the two sections.

FIG. 7 is a fragmentary longitudinal vertical sectional view showing the male section spokes as having pivoted to substantially-coaxial retracted positions, and further showing the male section as being received within an insertion sleeve.

FIG. 8 is a fragmentary longitudinal vertical sectional view showing the female section spokes as having been pivoted to substantially-coaxial retracted positions, and further showing the female section as being received within an insertion sleeve.

FIG. 9 is a fragmentary longitudinal vertical sectional view of the conical cutter head, this view showing such head in its closed ready-to-cut position.

FIG. 10 is a view similar to FIG. 9, but shows the cutter head as having been moved to its opened ready-to-withdraw position, and further shows the opened cutter head as having been moved leftwardly relative to the stylet.

FIG. 11 is a schematic view showing the closed cutter head as being arranged within a patient's vena cava, and as being directed toward a portion thereof behind which the portal vein is located.

FIG. 12 is a schematic view, generally similar to FIG. 11, but shows the cutter head as having been advanced and as penetrating the proximate walls of the vena cava and the portal vein.

FIG. 13 is a schematic view, generally similar to FIG. 12, and shows the guide stylet as penetrating the opening between the vena cava and the portal vein, and further shows the cutter head as having been moved to its opened position and as being arranged within the vena cava during withdrawal from the patient.

FIG. 14 is a schematic view, generally similar to FIG. 13, and shows the insertion sleeve containing the folded female section as being guided along the stylet and as penetrating the opening.

FIG. 15 is a schematic view, generally similar to FIG. 14, and shows the female section as having been ejected from the insertion sleeve along the guide stylet so as to be positioned within the portal vein, with its spokes having been moved to their substantially-radial outward positions.

FIG. 16 is a schematic view, generally similar to FIG. 15, and shows the female section, with its spokes expanded, as having been pulled back so that the spokes engage a marginal portion of the portal vein about the opening, with the insertion sleeve being withdrawn through the vena cava along the stylet.

FIG. 17 is a schematic view, generally similar to FIG. 16, and shows the male section as having been ejected from the insertion sleeve in the vena cava, and further showing its spokes has having moved to their expanded outward positions.

FIG. 18 is a schematic view, generally similar to FIG. 17, showing the male and female sections as having been operatively coupled together so that the expanded spokes of the male and female sections engage marginal portions of the vena cava and portal vein, respectively, immediately about the opening therebetween, and further showing the stylet as still penetrating the assembled shunt.

FIG. 19 is a schematic view, generally similar to FIG. 18, showing the stylet as having been withdrawn through the vena cava and shows the assembled shunt as providing an anastomosis between the vena cava and the portal vein to relieve portal hypertension.

MODE(S) OF CARRYING OUT THE INVENTION

At the outset, it should be clearly understood that like reference numerals are intended to identify the same structural elements, portions or surfaces consistently throughout the several drawing figures, as such elements, portions or surfaces may be further described or explained by the entire written specification of which this detailed description is an integral part. Unless otherwise indicated, the drawings are intended to be read (e.g., arrangement of parts, mounting, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.) simply refer to the orientation of the illustrated structure as the particular drawing figure faces the reader. Unless otherwise indicated, the terms "inwardly" and "outwardly" refer to the orientation of a surface relative to its axis of elongation, or axis or rotation, as appropriate.

Referring now to the drawings, and, more particularly, to FIGS. 1-8 thereof, this invention broadly provides an improved shunt, of which a presently-preferred embodiment is generally indicated at 20, for providing an anastomosis (i.e., a surgical joining of two hollow blood vessels or other tubular organs). The invention is deemed to have particular utility to provide an anastomotic shunt between a patient's vena cava and his portal vein, so as to relieve an excess pressure condition within the portal vein (i.e., portal hypertension). Thus, in FIG. 1, the improved shunt is shown as being provided within aligned openings 21,22 provided in the patient's vena cava 23 and portal vein 24, respectively. However, the invention is not limited to this particular end use, and possesses general utility to provide a shunt or anastomosis between other blood vessels (i.e., both venous and arterial), ducts, and passageways as well. Thus, while the invention will now be described in the environment of relieving portal hypertension, it should be clearly understood that the scope of the appended claims are not limited to this particular use, unless an explicit limitation to that effect appears therein.

The illustrated form 20 of the improved shunt is shown as including a leftward male section 25 and a rightward female section 26. Male section 25 is shown as being a thin-walled cylindrical tube having a horizontal axis x—x. The male section has an annular vertical left end face 28, an annular vertical right end face 29, and inwardly -and outwardly-facing horizontal cylindrical surfaces 30,31, respectively, extending between end faces 28,29. As best shown in FIGS. 4 and 6, four blind tapped holes, severally indicated at 32, extended horizontally into the male section from its right end face 29. These four holes are spaced from one another by equal arc distances of 90°. In FIG. 4, these four holes are specifically shown as being arranged at the 1:30, 4:30, 7:30 and 10:30 o'clock positions.

As best shown in FIG. 1, four blind concave slots, severally indicated at 33, extend radially into the male section from its outer cylindrical surface 31 adjacent left end face 28. In FIG. 3, these slots are shown as being arranged in the 12:00, 3:00, 6:00 and 9:00 o'clock positions, and are therefore spaced equally from one another by intermediate are distances of 90°. Each slot is shown as having transversely-spaced parallel planar chordal side surfaces, and an outwardly-facing concave bottom surface. The bottom surface may be configured as a cylindrical segment, and the slots may be formed by plunging a cylindrical milling head radially into the male section at the locations shown. As best shown in FIG. 3, a hole, indicated at 34, extends through the wall portion of each section so as to normally intersect the planar side surfaces of each slot. V-shaped spoke assemblies, generally indicated at 35, have their apexes positioned within recesses 33, with their individual spokes 36 extending outwardly from a hollow tubular apex 38. In the illustrated form, each spoke is arranged at an angle of about 15° with respect to a radial line drawn through the apex at the angular positions indicated. Hence, the spokes of any assembly are arranged at an acute included angle of about 30° with respect to one another. In the preferred embodiment, one spoke assembly is arranged in each of the four male section recesses 33. Hence, there are a total of eight individual spokes 36 extending outwardly from the male section, and these are arranged in cooperative pairs spaced from one another by a 30° included angle. Each spoke assembly may be formed of a length of relatively-stiff surgical wire or the like. If desired, the apex may be formed to have several spring-like helical convolutions (not shown) wound therein.

A cylindrical pin 39 is arranged in each of holes 34, and has a central portion penetrating the apex of the associated spoke assembly. Hence, each spoke assembly is mounted on the male section for pivotal movement about the axis of the associated pin. As shown in FIG. 1, when the spokes extend outwardly from the male section in a plane substantially perpendicular to axis x—x, portions of the spoke assembly in the vicinity of the apex engage the concave bottom surface of the associated slot to prevent further rotation of the spoke assemblies in an outward direction away from surface 31. These spokes may, however, be rotated in the opposite direction so as to lay along-side the male section outer surface 31, as shown in FIG. 7. However, as the spokes are rotated in this direction, a portion of each spoke just outward of the apex, will engage the curved edge formed by the juncture of the slot concave bottom surface with the outer surface 31. Thus, this engagement will preclude the spokes from being rotated to a position at which the spokes simply lie against surface 31. Rather, the engagement just described will cause the spokes to lie at an acute included angle of about 10°-20° with respect to a coaxial line in surface 31. Hence, to move the distal ends of the spokes so as to lie along surface 31, the spokes must be flexed or bent inwardly, as described infra. This feature is desirable because the spokes will be biased to move outwardly from their contracted positions (i.e., as shown in FIG. 7) to their expanded positions (i.e., as shown in FIGS. 1 and 2) when the male section is ejected from its insertion sleeve.

Female section 26 is substantially a mirror image of the male section. Hence, the prime of the reference numeral used with respect to the male section, has been used to describe the corresponding part or portion of the female section. The only salient difference between the two sections is that tapped blind holes 32' in the female section are of greater depth than holes 32 in the male section, as shown in FIG. 6. The spokes 36' on the female section are also movable between extended positions (i.e., as shown in FIGS. 1 and 2) and retracted positions (i.e., as shown in FIG. 8).

As clearly shown in FIG. 6, four connection studs, severally indicated at 40, are received in male section holes 32 so as to have exposed portions alignable with female section holes 32'. Each mounting stud has an externally-threaded left marginal end portion matingly received in a male section hole 32, has an intermediate shank portion, and has a rightwardmost hook portion 41 adapted to enter an aligned female section hole 32'. This hook portion has leftwardly-facing barbs or catch surfaces at its distal end which are adapted to lockingly engage the internal threads of female section holes 32' when the sections are pushed together. Moreover, these arrowhead-like barbs act somewhat as a ratchet, in that it will allow the male and female sections to be pushed axially together but will preclude them from being pulled apart. These studs serve two principal purposes. First, they provide a means by which the male and female sections may be joined together in a ratchet-like manner. Secondly, they also serve to require that the male and female sections are rotationally oriented relative to one another (i.e., with the corresponding spokes of the two sections lying in common planes) prior to the sections being joined together.

As shown in FIG. 7, the male section spokes 36 are adapted to be moved toward their retracted positions by first overcoming the opposing opening bias created by the contact between the spokes and the intersection of recesses 33 with male section outer surface 31. Once the spokes have been moved to their retracted positions, the male section may be inserted into a protective sheath, generally indicated at 42. This sheath is shown, in pertinent part, as being a thin-walled cylindrical tube having inwardly -and outwardly-facing horizontal cylindrical surfaces 43,44, respectively, and an annular vertical right end face 45. Sleeve inner surface 43 is of a diameter only slightly greater than the diameter of the retracted spokes. However, the spokes are bowed or flexed outwardly into engagement with sleeve inner surface 43. In any event, sleeve 42 contains a tubular plunger, a portion of which is indicated at 46. This plunger is shown as also being a cylindrical tube having, in pertinent part, an outer cylindrical surface 48 arranged to slidably engage sleeve inner surface 43, an inner cylindrical surface 49, and an annular vertical right end face 50. Sleeve 42 and plunger 46 are connected via suitable stylets (not shown) such that the insertion sleeve may be inserted into the patient's body along a path defined by guide stylet 51, described infra, to a desired position which may be determined by a fluoroscope or the like. Once the sleeve is in the proper position, the insertion sleeve stylets may be moved relative to one another to selectively push out or eject the male section through the open right end of the sleeve. After the male section has been so ejected, nothing will hold the spokes in their retracted positions, and the flexure of same will bias the spokes to move outwardly toward their expanded positions.

As best shown in FIG. 8, the female section 22 is similarly adapted to be enclosed within a protective sheath, which is indicated as being the same as sheath 42. The only salient difference is that the male and female sections are loaded into the sheath in opposite directions; that is, plunger right end face 50 is adapted to engage the left end face of the male section (i.e., as shown in FIG. 7), but is adapted to engage the distal ends of spokes 36' of the female section (i.e., as shown in FIG. 8)

Referring now to FIGS. 9 and 10, the invention also provides an improved cutter or punch, generally indicated at 52, which is adapted to be selectively inserted into one of the vessels, such as the patient's vena cava, and manipulated so as to punch or cut a hole between the juxtaposed walls of the adjacent vessels. Cutter 52 is adapted to be selectively moved between a closed ready-to-cut position, (i.e., as shown in FIG. 9), and an opened ready-to-withdraw position, (i.e., as shown in FIG. 10), via a somewhat clamshell-like action. The cutter has two conically-segmented sections 53,54 which, when closed (FIG. 9), generally simulate a cone having a sharpened tip or apex 55. These two sections are mounted on two concentric tubular stylets 56,58, respectively. The leftward or rear end of the cutter sections are mounted on outer stylet 56 via links 59,59. Each link has an outer marginal end portion pivotally connected to a rear end to the appropriate cutter section, and has an inner marginal end portion pivotally connected to the right marginal end portion of outer stylet 56. Intermediate portions of cone sections 53,54 are connected to the right marginal end portion of the inner stylet 56 by links 60,60. Links 60,60 have their outer ends pivotally connected to intermediate portions of cone sections 53,54, and have their inner marginal end portions pivotally connected to the right marginal end portion of the inner stylet 58 between stylet end faces 61,62.

The inner stylet 58 is shown as terminating in an annular vertical right end face 61, which extends beyond the right end face 62 of the outer stylet. Moreover, guide stylet 51 is shown as slidably penetrating the inner stylet and as terminating in a spherical ball 63, which prevents stylet 51 from being withdrawn through the inner stylet. Thus, as shown in FIG. 9, as the cutter 52 is inserted into the body, it carries with it the right marginal end portion of stylet 51. Thus, by selective relative movement of cutter stylets 56,58, the cutter may be selectively moved between its closed and opened positions. As comparatively illustrated in FIGS. 9 and 10, when the cutter is in its closed position (i.e., as shown in FIG. 9), the cutter has a relatively large diameter $D_1$. When the cutter is moved to its opened position, however, the pivotal action of conical segments 53,54, causes the cutter to have a smaller diameter $D_2$. Thus, the cutter may be moved to its closed position and advanced to punch or cut a hole of diameter $D_1$ through the vessel(s), and then moved to its opened position of reduced diameter $D_2$ to permit the cutter to be readily and easily withdrawn through the vessel opening just formed.

Operation

The method of operation of the improved device is to provide a postal-caval shunt is comparatively illustrated in FIGS. 11–19.

FIG. 11 illustrates a portion of the portal vein as lying closely along side a portion of the patient's vena cava. The flow of blood through these two vessels is first temporarily occluded, such as by means of a double-balloon catheter (not shown). This device is itself well-known. Basically, a catheter containing two axially-spaced balloons in their collapsed positions, is inserted longitudinally into the appropriate blood vessel to the desired location. Thereafter, the balloons are selectively inflated so as to engage the vessel walls. Being axially-spaced, the balloons thus form a sealed chamber therebetween when inflated. Suitable passages and lumens are provided to permit additional catheters and catheter-like members to enter the space between the two balloons. As indicated above, double-balloon catheters are first inserted into the patent's vena cava and portal vein. The balloons of these catheters are then inflated to temporarily occlude the flow of blood in these vessels at the site of the proposed anastomosis. As shown in FIG. 11, the cutter 52, in the closed position, is inserted into this chamber, and is directed toward the portion of the vena cava wall against which the portion of the portal vein is juxtapositioned.

As shown in FIG. 12, the cutter 52 is then caused to punch or cut a hole between such proximate vessel wall portions. As the cutter penetrates these two walls, it carries the forward end of stylet 51 with it. However, this end of the stylet is protectively enclosed by the two cutter sections.

As shown in FIG. 13, after openings 21,22 have been made in the vena cava and portal vein, the cutter is then moved to its open position, and is withdrawn along stylet 52 back through the vena cava, and is withdrawn from the patient's body. It should also be noted that stylet 51, which acts as a guide for subsequent steps, remains within opening 21,22.

As shown in FIG. 14, female section 26 is first positioned within insertion sleeve 42 (i.e., as shown in FIG. 8). Thereafter, this insertion sleeve is slipped over the proximate marginal end portion of guide wire 51, and is moved therealong to penetrate openings 21,22.

After the insertion sleeve has penetrated these openings, plunger 46 is then moved to expel the female section from the insertion sleeve within the patient's portal vein. The female section is still penetrated by guide wire 51. When the female section is ejected from the insertion sleeve, its spokes, which have been held in a retracted position against the overcoming bias of their flexure) will immediately expand outwardly to their expanded positions, as shown in FIG. 15. Thereafter, the insertion sleeve may be withdrawn along stylet 51, leaving female section 26 in the portal vein but penetrated by guide wire 51. The male section is then inserted into the insertion sleeve, and the assembly thus formed is moved along guide wire 51 into the patient's vena cava. Once in position, the male section is then ejected from the insertion sleeve. As this happens, its spokes move to their outward positions, as shown in FIG. 17. Thereafter, the surgeon removes the insertion sleeve 42 along stylet 51.

Thus, up to this point, stylet 51 has functioned as a guide along which the various insertion sleeves and sections have been inserted and withdrawn, respectively. The surgeon may then insert a catheter containing a J-hook (not shown) or the like and, with the aid of suitable fluoroscopic techniques, may selectively rotate the male and female sections to desired relative angular positions at which connecting studs 41 are aligned with female section recesses 32'. Thereafter, and, again by means of a J-hook or equivalent, the surgeon may operatively cause these two sections to move toward one another, with barbed end portions 41 of the mounting studs penetrating female section openings 32', thereby holding the male and female sections together. As previously noted, when the sections are coupled together, the spokes of the two sections are aligned with respect to one another for purpose discussed infra.

Thereafter, stylet 51 is withdrawn through the patient's vena cava, leaving the shunt 20 to provide an anastomosis between the portal vein and vena cava. Hence, excess pressure in the portal vein (i.e., portal hypertension) may drain through the opening provided by shunt into the patient's vena cava, thereby relieving such excess portal hypertension. If, however, the size of the opening provided within the shunt, must be enlarged, the surgeon may, by means of a laser or the like, cut away triangular- or trapezoidal-shaped portions between the spokes of the male and female sections to provide for increased flow of blood from one vessel to the other.

Therefore, the present invention provides an improved method and apparatus for providing an anastomotic shunt, which avoids the need for major surgery. As noted above, the improved shunt is deemed particularly useful to relieve a portal hypertension condition. The invention is not, however, limited to this particular use.

Modifications

The present invention contemplates that many changes and modifications may be made. For example, the number, size and spacing of the various spokes, as well as their manner of attachment to the associated section, may be readily changed. Similarly, while the spokes of each cooperative pair are disposed at an acute included angle of about 30° in the preferred embodiment, this angle may be readily changed or modified. The spokes may be formed integrally with, or separately from, the associated section. Preferably, the spokes are biased to move to their outward positions such that this occurs automatically upon ejection from the insertion sleeve. However, this is not invariable. If desired, the spokes may be manually moved to their extended positions.

The means for connecting the two sections, as shown to be a ratchet-like mechanism in the preferred embodiment, may be changed as desired. Other forms of connecting devices might be alternatively employed. Similarly, while it is presently desired that the spokes of the respective sections be aligned with one another so as to permit the surgeon the opportunity to enlarge the shunt by means of laser surgery, should the need exist, this arrangement is not invariable. Such spokes need not be aligned, if desired.

Similarly, the cutter head may take other forms as well. The disclosed form is preferred since the effective diameter of the cutter head may be reduced so as to facilitate its withdrawal through the opening. On the other hand, other types of cutters and punches might alternatively be employed.

Therefore, while a preferred form of the improved apparatus has been shown and described, and several modifications thereof discussed, persons skilled in this art will readily appreciate that various additional changes and modifications may be made without departing from the spirit of the invention, as defined and differentiated by the following claims:

I claim:

1. An anastomotic shunt, comprising:
   an open-ended tubular male section;
   an open-ended tubular female section;
   each of said sections having a plurality of spokes, each of said spokes adapted to be moved between an extended position at which said spoke extends outwardly from the associated section, and a retracted position at which said spoke is positioned along side the associated section; and
   joining means for joining said sections together so as to create a passageway therewithin;
   whereby said sections may be positioned in an opening joining two tubular vessels and may be joined together with said spokes being in said extended positions to hold marginal portions of said vessels about said openings together to provide a shunt therebetween.

2. An anastomotic shunt as set forth in claim 1 wherein said spokes are pivotally mounted on the associated section for movement between said positions.

3. An anastomotic shunt as set forth in claim 1 wherein said spokes are biased to move towards an extended positions.

4. An anastomotic shunt as set forth in claim 1 and further comprising a V-shaped spoke assembly having its apex pivotally mounted on the associated section and having a pair of said spokes extending away from said apex.

5. An anastomotic shunt as set forth in claim 4 wherein said spokes extend outwardly from said apex at an acute included angle of about 30°.

6. An anastomotic shunt as set forth in claim 4 wherein said spoke assembly is a wire-form member having a plurality of tubular convolutions at said apex.

7. An anastomotic shunt as set forth in claim 6 and further comprising a pin mounted on the associated section and having an intermediate portion passed through said convolutions.

8. An anastomotic shunt as set forth in claim 1 wherein eight of said spokes are mounted on each section.

9. An anastomotic shunt as set forth in claim 1 wherein each of said sections is configured as a thin-walled cylinder.

10. An anastomotic shunt as set forth in claim 1 wherein said joining means includes a plurality of holes provided in said male section, a corresponding plurality of studs mounted in said male section holes, each of said studs having a catch member located at its distal end, a plurality of holes provided in said female section, each female section being adapted to receive insertion of the distal end of one of said studs.

11. An anastomotic shunt as set forth in claim 10 wherein said catch member is configured to permit said sections to be pushed together, but to prevent said sections from being pulled apart.

12. An anastomotic shunt as set forth in claim 11 wherein each female section hole is internally threaded to receive insertion of said stud distal end portion in a ratchet-like manner.

13. A anastomotic shunt as set forth in claim 10 and further comprising multiple studs and multiple holes provided in said male and female sections to permit said sections to be radially aligned prior to being joined together.

14. An anastomotic shunt set forth in claim 1 wherein the spokes of said sections are aligned with one another, when said sections are joined together.

15. The method of providing an anastomotic shunt between two tubular vessels, comprising the steps of:
   inserting a cutter head through one of said vessels;
   pushing said cutter head and a stylet carried thereby through the walls of said vessels to provide openings therein;
   withdrawing said cutter head along said stylet;
   positioning a first member having a plurality of spokes mounted for movement between exteded positions and retracted positions, on said stylet;
   holding said first member spokes in said retracted positions;
   inserting said first member along said stylet through said one vessel and through said openings into the other vessel;
   moving said first member spokes to their extended positions;
   positioning a second member having a plurality of spokes mounted for movement between extended positions and retracted positions on said stylet;
   holding said second member spokes in said retracted positions;
   inserting said second member along said stylet through said one vessel;
   moving said second member spokes to said extended positions in said one vessel;
   joining said first and second members together such that marginal portions of said vessels about said openings will be held together by said spokes; and
   removing said stylet;

thereby to form an anastomotic shunt between said vessels.

16. The method as set forth in claim 15 wherein the step of withdrawing said cutter head includes the further step of reducing the effective transverse size of said cutter head.

17. The method as set forth in claim 15 and further comprising the step of aligning the spokes of each section prior to joining said sections together.

18. The method as set forth in claim 15 and further comprising the step of forming additional openings between said spokes to increase the size of said shunt.

* * * * *